United States Patent
Schmidt et al.

(10) Patent No.: US 12,222,338 B2
(45) Date of Patent: Feb. 11, 2025

(54) GAS ANALYZER WITH IMPROVED ARCHITECTURE FOR OPERATION IN POTENTIALLY HAZARDOUS ENVIRONMENTS

(71) Applicant: Gas Chromatography Systems MAXUM GmbH, Karlsruhe (DE)

(72) Inventors: Glen Eugene Schmidt, Bartlesville, OK (US); Thomas Neuhauser, Cypress, TX (US)

(73) Assignee: GAS CHROMATOGRAPHY SYSTEMS MAXUM GMBH, Karlsruhe (DE)

( * ) Notice: Subject to any disclaimer, the term of this patent is extended or adjusted under 35 U.S.C. 154(b) by 0 days.

(21) Appl. No.: 18/695,448

(22) PCT Filed: Aug. 31, 2022

(86) PCT No.: PCT/IB2022/058162
§ 371 (c)(1),
(2) Date: Mar. 26, 2024

(87) PCT Pub. No.: WO2023/052870
PCT Pub. Date: Apr. 6, 2023

(65) Prior Publication Data
US 2024/0329014 A1    Oct. 3, 2024

(30) Foreign Application Priority Data

Sep. 30, 2021 (WO) .................. PCT/IB2021/058985

(51) Int. Cl.
*G01N 30/32* (2006.01)
*G01N 30/02* (2006.01)
*G01N 30/86* (2006.01)

(52) U.S. Cl.
CPC ......... *G01N 30/32* (2013.01); *G01N 30/8693* (2013.01); *G01N 2030/025* (2013.01); *G01N 2030/328* (2013.01)

(58) Field of Classification Search
CPC ............. G01N 2030/025; G01N 30/32; G01N 2030/328; G01N 30/30; G05D 16/2022;
(Continued)

(56) References Cited

U.S. PATENT DOCUMENTS 4,553,985 A * 11/1985 Dahlgren ............... G01N 30/38
95/82
5,524,084 A * 6/1996 Wang ........................ G01F 1/34
702/100

(Continued)

FOREIGN PATENT DOCUMENTS

EP    3627274 A1    3/2020
EP    3627274 B1    10/2020
(Continued)

OTHER PUBLICATIONS

PCT International Search Report and Written Opinion of International Searching Authority dated Nov. 18, 2022 corresponding to PCT International Application No. PCT/IB2022/058162 filed Aug. 31, 2022.

*Primary Examiner* — Kristina M Deherrera
*Assistant Examiner* — Gedeon M Kidanu
(74) *Attorney, Agent, or Firm* — Oliff PLC

(57) ABSTRACT

A gas analyzer includes a self-contained pressure module that at least partly encloses a tube for a gas, wherein a pressure module is equipped with a sensor and a valve, the sensor and the valve are operable through a master control circuit that is accommodated in a self-contained control enclosure outside of the pressure module, separate from the valve and the sensor.

19 Claims, 3 Drawing Sheets

(58) Field of Classification Search
CPC ............ G05D 16/2013; G05D 16/206; G05D 16/2024; G05D 7/0635; G01F 1/34; G01L 19/0084; G05B 19/0423; G05B 2219/31369; G05B 23/0283; B01L 2400/0666; B64D 2045/0085; B64F 5/60; F16K 27/12; H04L 63/02; H04L 67/125; H04L 69/08; H04L 69/14; H04L 69/18; H04Q 2209/70; H04Q 9/00

See application file for complete search history.

(56) References Cited

U.S. PATENT DOCUMENTS

| | | | |
|---|---|---|---|
| 10,670,054 B2* | 6/2020 | Cohen | F15B 5/006 |
| 11,215,588 B2 | 1/2022 | Schmidt et al. | |
| 2017/0286572 A1 | 10/2017 | Hershey et al. | |
| 2019/0313164 A1 | 10/2019 | Bragg | |
| 2020/0096487 A1* | 3/2020 | Schmidt | G05D 16/206 |
| 2020/0103378 A1* | 4/2020 | Schmidt | G01N 30/62 |
| 2021/0294359 A1 | 9/2021 | Strauch | |

FOREIGN PATENT DOCUMENTS

| | | |
|---|---|---|
| EP | 3882737 | 9/2021 |
| WO | 2012021681 | 2/2012 |

\* cited by examiner

GAS ANALYZER WITH IMPROVED ARCHITECTURE FOR OPERATION IN POTENTIALLY HAZARDOUS ENVIRONMENTS

CROSS-REFERENCE TO RELATED APPLICATIONS

This is a U.S. national stage of application No. PCT/IB2022/058162 filed 31 Aug. 2022. Priority is claimed on World Intellectual Property Application No. PCT/IB2021/058985 filed 30 Sep. 2021, the content of which is incorporated herein by reference in its entirety.

BACKGROUND OF THE INVENTION

1. Field of the Invention

The invention relates to a gas analyzer with an improved architecture for operation in a potentially hazardous environment.

2. Description of the Related Art

EP 3 627 274 B1 discloses a fluid pressure control apparatus for a gas chromatograph that comprises a solenoid valve, which can be actuated through an electronic controller, and pressure sensor. The fluid pressure control apparatus is structured to meet an intrinsic safety standard, such as International Electrotechnical Commission (IEC) 60079-11. The electronic controller is accommodated in a housing that encloses the valve with its solenoids and the pressure sensor. Portions of a pipe for transporting gases like hydrogen pass through the housing and are connected through fittings.

Moreover, EP 3 882 737 A1 teaches a gas chromatograph that comprises an explosion-proof housing that connects to a manifold block, through which a gas, hydrogen, e.g., is transported in a tube. The manifold block encloses the valve portion of a valve and a pressure sensor. A solenoid portion of the valve is accommodated in the adjacent explosion-proof housing.

WO 2012/021681 A1 discloses an intrinsically safe thermal conductivity detector for a process gas chromatograph. The detector comprises a thermistor, a reference resistor connected to the thermistor and an operational amplifier configured to drive a voltage through the reference resistor onto the thermistor. The detector further comprises an infallible resistance element connected between the thermistor and a high impedance input of the operational amplifier.

Gas analyzers, in particular gas chromatographs, are used for measuring the component makeup of gases and liquids like that are utilized in chemical production processes or natural gas coming from a gas well. For detecting different kinds of components, different supply and carrier gases are used, including combustible or potentially hazardous gases like hydrogen or other gases such as nitrogen, helium or argon and air. At the same time, there is demand for more efficient safety for the operation of gas analyzers. In addition to that, gas analyzers must be reliable and cost-effective.

SUMMARY OF THE INVENTION

It is an object of the invention to provide a gas analyzer that offers an improvement in at least one of these aspects in comparison to convention gas analyzers.

This and other objects and advantages are achieved in accordance with the invention by a gas analyzer comprising a pressure module through which a gas is to be transported. The pressure module at least partly encloses a tube, through which the gas flows during operation of the gas analyzer. The pressure module is self-contained. Gas only enters or exits the pressure module only through fittings provided for that purpose. Thus the pressure module may be configured to maintain a gas pressure on its inside that is not affected by an ambient pressure. The gas transported through the tube may be a carrier gas or another supply gas. Particularly, the gas may be hydrogen or any other gas that can form an explosive mixture with air, or gases like helium, nitrogen, argon or air. Furthermore, the gas analyzer comprises at least one sensor that is accommodated in the pressure module. The at least one sensor is configured to measure a physical quantity inside the pressure module and/or the tube. Moreover, the gas analyzer comprises at least one valve that is configured to control a gas flow through the tube. The valve and the sensor are operable through a master control circuit. The master control circuit is configured to define setpoints, for example, for a closed loop control circuit accommodated in the pressure module. This closed loop control circuit may be configured for reading measurement data from the sensor and for actuating the valve respectively.

In combination, they are suitable to reliably control the gas flow through the tube depending on the present operational situation of the gas analyzer.

Particularly, the valve and the sensor may be configured to govern a gas flow to a subsequent component of the gas analyzer, e.g., a separation column.

In accordance with the present invention, the master control circuit is accommodated in a self-contained control enclosure that is located separate from the pressure module. Thus, the control enclosure separates the master control circuit from the valve and the sensor, which are accommodated in the pressure module. Such a separate accommodation of these components allows economical installation even in potentially hazardous areas.

In turn, potentially hazardous supply gases like hydrogen are separated from the control enclosure in a reliable and cost-effective manner.

Additionally, the gas analyzer can use control circuits, especially master control circuits, with more energy-demanding functions, like processing of measurement data or execution of computer programs on the master control circuit. The master control circuit is placed in the control enclosure and separated from an atmosphere where hazardous gases may occur and separated from the pressure module, which is purposed to control flow of even flammable supply gases. As a result, potentially flammable supply gases are not conducted into the control enclosure. Furthermore, requirements for cost effective measures to operate the gas analyzer can be met. That allows for manufacturing and operating the gas analyzer in a cost-effective manner. Altogether, the gas analyzer in accordance with the present invention shows an appropriate safety level, a wider variety of additional data processing functions, and is cost-effective to produce and operate.

In an embodiment of the inventive gas analyzer, one or more valves are at least partly accommodated in an encapsulation. The encapsulation is configured to engulf at least a portion of the valve where a significant amount of energy is stored. Through the encapsulation, an outer atmosphere that might contain potentially flammable gases is kept from reaching the solenoid portion of the valve.

The encapsulation may be formed as a casting compound that is an electric insulator, especially a resin, a thermoplastic material or a comparable material. Such an encapsulation is cost-effective to manufacture. Moreover, the encapsulation with the at least partly engulfed valve may be accommodated inside the pressure module or outside of it. Alternatively, the valve may be at least partially accommodated in a molding.

Furthermore, the valves may at least partly be placed outside of the pressure module. A placement of the valves as a part of the pressure module outside of the control enclosure decreases heat dissipation from valves within the control enclosure. This allows operation in a broader range of ambient temperature.

In addition to that, the master control circuit of the inventive gas analyzer may comprise at least one intrinsic safety barrier circuit. The intrinsic safety barrier circuit is configured to connect to at the least one sensor and the valve. Particularly, the intrinsic safety barrier circuit serves to supply limited energy to a closed control circuit, which controls the valve and the at least one sensor. Moreover, the intrinsic safety barrier circuit is configured to facilitate a data transfer between the master control circuit and the closed loop control circuit, comprised of at least one sensor and/or the at least one valve. This allows for actuating the at least one valve, reading measurement data from the at least one sensor and/or calibrating either of them. The intrinsic safety barrier circuit comprises 15 passive electronic components, especially diodes, Zener diodes and fuses, which are configured to limit the energy supplied to the pressure module to a fixed maximum energy value. A fixed maximum voltage and current limitation is chosen to ensure that intrinsically safety conditions are met. The intrinsic safety barrier circuit allows for supplying a sufficient amount of energy to the at least one sensor and to the at least one valve. In a preferred embodiment of the invention, the intrinsic safety barrier circuit may be configured in accordance with the IEC 60079-11 standard. The disclosed intrinsic safety barrier circuit is at least partly made of passive electronic components. As a result, it can be manufactured in a cost-effective manner and shows a high degree of reliability.

In another embodiment of the present invention, the pressure module in combination with the valve and the at least one sensor is configured such that requirements regarding safe operation can be met.

The gas analyzer shows a safety level on par with existing protection standards for gas chromatographs while omitting the use of heavy sophisticated components like metal housings or enclosures for the pressure module.

For example, the pressure module may be structured to withstand operational internal pressures of up to 15 bar. Operational internal pressures of up to 15 bar are commonly not considered to meet the requirements of explosion protection as outlined in various standards. Thus, the pressure module is to be construed as a non-explosion-protected enclosure in comparison to other conventional gas chromatographs. Therefore, the pressure module may be formed as a relatively simple, light and cost-effective enclosure. Having such an enclosure as the pressure module allows for simplifying the overall configuration of the inventive gas analyzer.

Moreover, the at least one sensor in the inventive gas analyzer can be a first pressure sensor. The first pressure sensor is exposed to a gas pressure that is present in the pressure module, especially a gas pressure close to the inlet of the pressure module. This may be used as an entrance pressure read. The gas pressure inside the pressure module is not immediately affected by an ambient pressure and thus serves as a sufficiently precise reference pressure. Thus, the first pressure sensor is configured to detect a depleting gas supply. The first pressure sensor may be attached to the tube upstream of the at least one valve. Thus, the first pressure sensor may be configured to measure a pressure in the gas that is supplied to the at least one valve.

Based on the pressure in the gas downstream of the at least one valve and its actuation, the pressure in the gas downstream of the at least one valve it adjusted. The pressure in the gas downstream of the at least one valve to a flow restriction defines the maximum flow of the gas that can be achieved downstream.

The pressure in the gas upstream of the at least one valve may be construed as an inlet manifold pressure of the tube. For the pressure of the gas upstream of the at least one valve, a simple measurement is sufficient. Thus, the first sensor may have an increased measuring inaccuracy. Such a simple sensor is cost-effective and is still sufficient to indicate if there is a sufficient supply pressure for the gas. This allows the implementation of a warning when the supply pressure of the gas falls below a critical threshold or other features recognizing or predicting failures rooted in the gas supply system.

Furthermore, information based on internal sensors such as the first pressure sensor is always available. Consequently, it may be used for operational procedures supporting reliable operation, e.g., shut down or startup procedures.

Due to the integration of the first pressure sensor into the pressure module significant efforts for integration, engineering and measures to achieve compatibility for external sensors are avoided. With such a first pressure sensor, the reliable and cost-effective operation of the inventive gas analyzer is facilitated.

Alternatively or additionally, the at least one sensor may comprise a temperature sensor. The temperature sensor is accommodated in the pressure module and is configured to measure a temperature there. The measured temperature is used as an input for a compensation function that is a part of a control program that operates the at least one valve. Based on this, the actuation of the at least one valve is adapted to adjust for thermal effects which affect the at least one sensor, e.g., the first pressure sensor, and/or the at least one valve. Furthermore, the pressure module may comprise a memory with a calibration data field for at least one of the sensors, especially the second pressure sensor, which allows for such a compensation function. Additionally, pressure variations may be compensated, too. Thus, the gas flow through the at least one valve may be precisely adjusted for a subsequent chromatographic analysis. Furthermore, the inventive gas chromatograph allows a thermal condition control in the pressure module to be omitted. As a result, the inventive gas analyzer does not need any temperature stabilizing devices and/or pressure stabilizing devices, which allows for a simple and cost-effective design and reliable operation.

Furthermore, the intrinsic safety barrier circuit comprises connectors for at least one, preferably at least four, more preferably at least six, further preferably, at least eight channels. Each channel is utilized to control a valve that governs the gas flow through a separate tube. This allows multiple doses of gas as a carrier gas or other supply gases to be supplied, which may each be used for a parallel chromatographic analysis or complex analytical solutions and combinations. The control functions of multiple channels may be concentrated in a single master control circuit. Among others, the invention is based on the surprising finding that a single master control circuit may provide sufficient power for multiple valves and sensors. The more channels the gas chromatograph encompasses, the more complex chromatographic analysis may be performed. The disclosed embodiments of the invention allows the versatility of a gas chromatograph to be increased without unduly increasing its dimensions while maintaining an increased safety level.

In another embodiment of the present invention, the intrinsic safety barrier circuit is configured to operate at a temperature of at least 85° C. The separation of the master control circuit from the at least one valve and the at least one sensor through the intrinsic safety barrier circuit allows for the use of more robust components for the intrinsic safety barrier circuit. Furthermore, the control program that encompasses the compensation for thermal effects on the tube has theoretically no operational limit. Thus, the disclosed gas chromatograph can also be operated at increased temperatures. This in turn allows for limiting or even omitting temperature stabilizing device in the inventive gas analyzer.

In yet another embodiment of the gas analyzer, the master control circuit is configured to provide at least 3.0 W of power. Preferable the control circuit may be configured to provide at least 6.0 W of power. Such power levels provide sufficient power for multiple valves and sensors in the pressure module or modules which may be operated simultaneously. Therefore, the inventive gas analyzer shows an enhanced degree of versatility and is suitable for further improvements or extensions.

The inventive gas analyzer may also comprise a second pressure sensor as one of the at least one sensor. The second pressure sensor is configured to measure a pressure in the tube which transports the gas. Moreover, the second pressure sensor is located downstream of the at least one valve. The second pressure sensor is located downstream of the at least one valve. As a result, the second pressure sensor is not subjected to pressure fluctuations in the inlet manifold pressure. The second pressure sensor is configured to be a part of a closed control loop with the at least one valve.

As the at least one valve is not subjected to pressure fluctuations in the inlet manifold, a closed control loop function of the closed control loop may omit any compensating functions for that and is able to obtain an increased precision. Furthermore, the second pressure sensor may be configured to be connected to a calibrated reference as a reference pressure. The reference pressure may be provided by a pressurized container. Compared to an ambient pressure as a reference pressure like atmosphere pressure, the calibrated reference is robust against fluctuations of ambient air pressure. Such fluctuations may occur when the gas analyzer is accommodated in a shelter, especially one with a purging system. Moreover, such fluctuations may be caused by an effluent collection system that is to carry away potential exhaust fluids from the gas analyzer, e.g., processed sample and carrier gas. Using such a calibrated reference pressure stabilizes the operation of the inventive gas analyzer and allows for reliably yielding exact measurements. The inventive gas analyzer offers an improved level of precision and is robust against unfavorable ambient conditions at the same time.

In another embodiment of the present invention, the second pressure sensor has a higher precision than the first pressure sensor. In this context, a higher precision is to be construed as having a smaller measurement error. The second pressure sensor may be a pressure sensor with a measurement error on the order of 100 ppm, whereas the first pressure sensor may be a pressure sensor with a measurement error of up to 5 percent. Due to this, the first pressure sensor may be formed as a simple and cost-efficient pressure sensor that serves to sense the inlet manifold of the pressure module and thus emulate a fixed pressure switch. In turn, the second pressure sensor is substantially insulated from pressure fluctuations in the inlet manifold and is capable of performing a pressure measurement with an increased precision. Complex compensators for pressure fluctuations may be omitted in the second pressure sensor. Thus, the disclosed embodiments of the present invention utilize the first and second pressure sensor in more appropriate manners and are also cost-effective.

The objects and advantages in accordance with the invention are also achieved by a method for simulating the operational behavior of a gas analyzer. In context with the disclosed method, the terms "gas analyzer" and "simulated gas analyzer" may be construed as being interchangeable. The operational behavior may comprise the progression of thermodynamic variables of a gas transported through it, e.g., its temperature, density, pressure, heat energy and/or enthalpy. It may also comprise combustion behavior, i.e., the ignition behavior of the gas, its burn rate, its volume expansion, its released heat energy and/or enthalpy. The method comprises a first step during which a set of data points is provided. The set of data points mirror the functioning of at least a portion of the gas analyzer that is to be simulated. The data points may mirror the structure of the respective portion of the gas analyzer or the entire gas analyzer. Particularly, the set of data points may constitute a so-called digital twin or may be part of a digital twin. The expression digital twin is to be construed in accordance with the US Pub. No. 2017/286572 A1, the content of which is incorporated herein by reference in its entirety. The set of data points may be provided by loading them into a memory of a computer upon which the disclosed method may be performed.

The disclosed method also comprises a second step in which at least one operational parameter of the gas analyzer is set. The operational parameter may comprise a condition under which the gas analyzer is operated, e.g., an ambient temperature. Additionally or alternatively, the operational parameter may comprise information about the analysis process that is to be simulated, e.g., which gas or gasses and in which amounts are to be utilized, the pressures, temperatures and/or flow rates at which the gas or the gasses are provided, and/or the duration of the operation. The second step may be performed by a user and/or through a data interface.

In addition, the disclosed method comprises a third step in which a computer program product is executed. The computer program product is configured to emulate the operational behavior of the gas analyzer based on the set of data points provided in the first step. The operational behavior is also emulated based on the at least one operational parameter provided in the second step. The set of data points and the operational parameter may be combined by the computer program product which emulates the operation, i.e., the operational behavior, of the gas analyzer under the circumstances defined in the first and second step. This emulated operation is also to be construed as a simulated operation. This serves for determining at least one performance parameter of the gas analyzer. The performance parameter describes information about events during the simulated operation that are yielded through the simulated operation of the simulated gas analyzer. For example, the performance parameter may comprise thermodynamic quantities such as the temperature, density and/or flow rate of a gas that exits a component of the simulated gas analyzer and/or an information about the composition of a gas mixture inside a component of the simulated gas analyzer. The performance parameter may also comprise information, whether a gas mixture has ignited during the simulated operation, under which conditions that ignition took place and/or information about a pressure increase caused by that ignition.

In a fourth step, the at least one performance parameter is output to a user and/or a data interface. The fourth step may utilize a suitable data connection to an output device readable by the user and/or to a different computer platform that may be configured to process the at least one performance parameter further. In accordance with the present invention, the gas analyzer simulated through the disclosed method is a gas analyzer in accordance with the disclosed embodiments. The features of the disclosed gas analyzer also apply to the disclosed method in a corresponding manner. Thus, the features of the gas analyzer in accordance with the disclosed embodiments also confer to the disclosed method.

The disclosed gas analyzer shows an increased level of safety because, among other reasons as well, its master control circuit is separated from it pressure module. Complex combustion calculations that include ignitions through sparks and the like may be omitted. Instead, the inventive method may only take into consideration self-ignition conditions for the gas or the mixture of gasses present in the pressure module. Particularly, the third step may be performed without taking into account ignitions by sparks and the like. This in turn allows for a significant simplification of the simulation performed based on the disclosed method. Therefore, the method in accordance with the invention allows for an accelerated simulation of the operational behavior of a gas analyzer that may be performed on a relatively simple hardware platform with a limited computing capacity. With the disclosed method, intended operations of a physical gas analyzer, that is as least partly mirrored by the set of data points, may be optimized faster. Particularly, a more comprehensive set of simulations may be performed in a reduced amount of time. The inventive gas analyzer also shows an improved aptitude for its own simulation, it may be operated in an efficient manner.

The objects and advantages in accordance with the invention are also achieved by a computer program product that is configured to simulate an operational behavior of a gas analyzer. Consequently, the computer program product may comprise code and/or instruction that cause a computer to perform the simulation of the operational behavior of the gas analyzer. In accordance with the present invention, the operational behavior is simulated through the method in accordance with the disclosed embodiments. The computer program product may comprise a set of data points that at least partly mirror the gas analyzer that is to be simulated. The computer program product may be a so-called digital twin, as described in US 2017/286572 A1. Furthermore, the computer program product may be stored in a machine-readable or computer-readable medium that is configured to interact with a computer. The computer program product may be embodied as software or in a hardwired form, e.g. a chip, an ASIC or an FPGA, or as a combination of software and a hardwired form. Furthermore, the computer program product may be formed as a monolithic program that is executed on a single hardware platform. Alternatively, the computer program product may be formed as modular software, comprising partial programs that are executed on separate hardware platforms and which interact with each other over a suitable data connection, e.g., an ethernet connection, an internet connection or a mobile data service.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the following, the present invention will be described in more detail in several figures. The figures are to be construed as mutually complementary. Particularly, identical numerals are to be construed as having the same technical meaning. The features of the embodiments shown in the figures may be combined with each other. Additionally, the features of the embodiments shown in the figures may also be combined with the embodiments outlined above, in which.

DETAILED DESCRIPTION OF THE EXEMPLARY EMBODIMENTS

Figure 1:
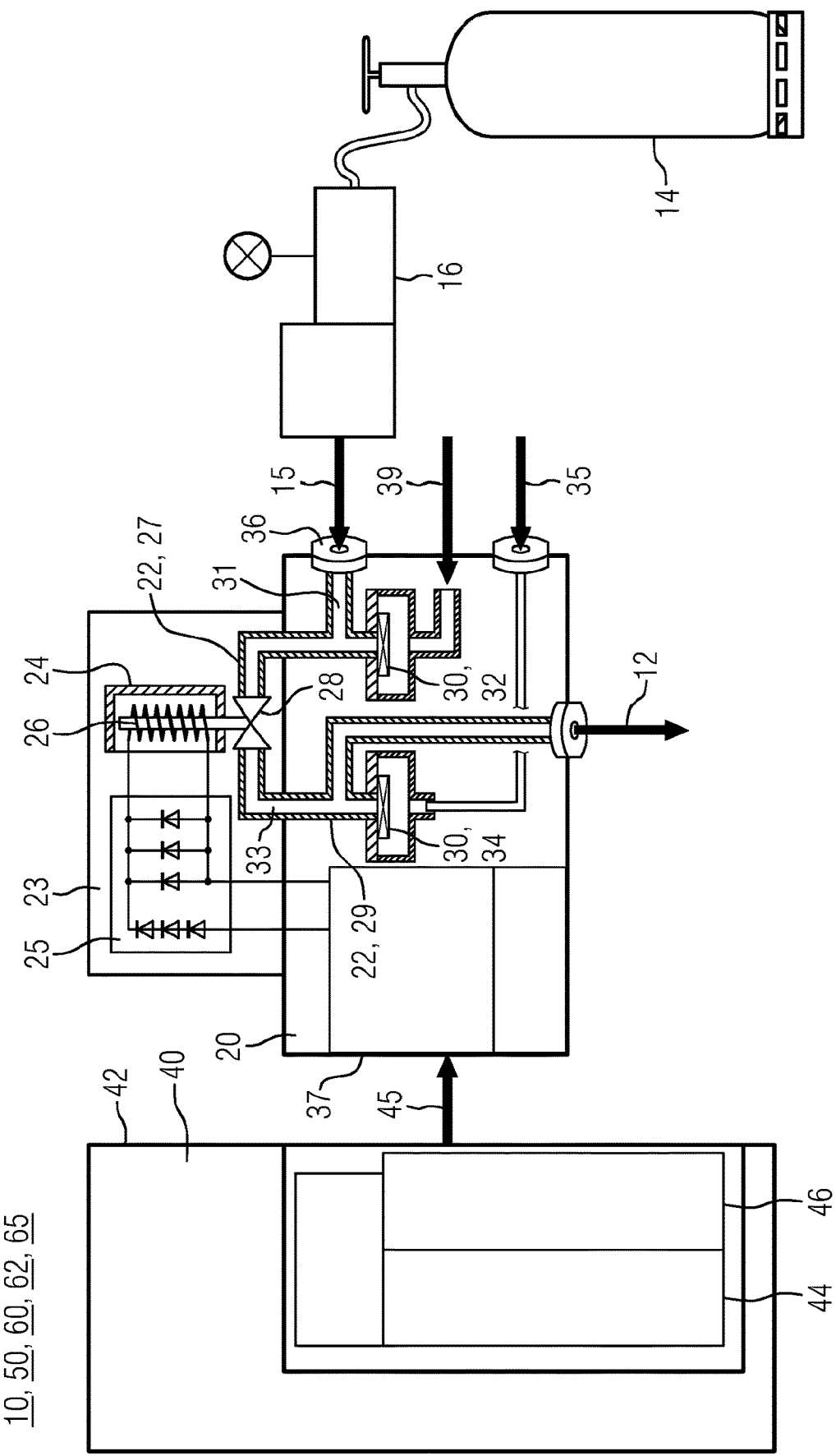
FIG. 1 a layout of a carrier gas supply unit in a first embodiment of the inventive gas analyzer.

FIG. 1 shows a carrier gas supply unit 50 that is utilized in a first embodiment of the claimed gas analyzer 10. The carrier gas supply unit 50 comprises a gas reservoir 14, which supplies a gas 15, e.g., hydrogen, that is to be fed to a separation column 12 (which is not shown in detail for purposes of clarity). The gas 15 from the gas reservoir 14 is fed through a pressure regulator 16 and into a pressure module 20, which encloses an upstream portion 27 of a pipe 22. The upstream portion 27 of the pipe 22 is connected to a fitting 36. The gas 15 in the upstream portion 27 of the pipe 22 is subjected to an upstream pressure 31, which is to be construed as an inlet manifold pressure. The upstream portion 27 of the pipe 22 is connected to a valve 24 that is potted in an encapsulation 23. The encapsulation 23 may be made of a resin, a thermoplastic material or any other castable material that is fit to provide an exclusion of the gas 15. The valve 24 comprises a valve portion 28 that constitutes a barrier between the upstream portion 27 of the pipe 22 and a downstream portion 29 of the pipe 22. The barrier may be actuated, i.e., opened or closed, through a solenoid portion 26 of the valve 24. The actuation of the solenoid portion 26 and therefore the valve 24 is controlled through a valve circuit 25 that is also potted in the encapsulation 23. The solenoid portion 26 may store a significant amount of energy that is capable of ignition. Consequently, the encapsulation 23 prevents the gas 15 in the pressure module 20 from getting to the solenoid portion 26, especially if the gas 15 is hydrogen. Thus, the encapsulation 23 constitutes a protector against explosions and increases the overall safety of the carrier gas supply unit 50 and the gas analyzer 10.

The downstream portion 29 of the pipe 22 discharges into the separation column 12 (which is not shown in detail in FIG. 1 for purposes of clarity). In the downstream portion 29 of the pipe 22, the gas 15 is subjected to a downstream pressure 33 that is regulated through the valve 24 and determines the pressure at which the gas 15 flows into the separation column 12. To this end, the pressure module 20 encompasses two sensors 30 that are formed as pressure sensors 32, 34. A first pressure sensor 32 is connected to the upstream portion 27 of the pipe 22 and is configured to measure the upstream pressure 31. The first pressure sensor 32 utilizes a gas pressure 39 inside the pressure module 20 as a reference pressure. Based on measurements by the first pressure sensor 32, the gas analyzer 10 is configured to detect a receding upstream pressure 31 and to indicate that the depleting gas reservoir 14 is to be replaced.

The valve 24 substantially shields the downstream portion 29 of the pipe 22 from fluctuations in the upstream pressure 31, which is to be construed as the inlet manifold pressure. During a normal operation of the carrier gas supply unit 50, the valve 24 is actuated to adjust the downstream pressure 33 to a predefined level. To this end, the downstream portion 29 of the pipe 22 is equipped with the second pressure sensor 34 that is arranged to measure the downstream pressure 33. The valve 24, the valve circuit 25 and the second pressure sensor 34 are configured to form a closed control loop that regulates the downstream pressure 33. Moreover, the second pressure sensor 34 is connected to a calibrated reference pressure 35. Utilizing such a calibrated reference pressure 35 allows for an even more precise adjustment of the downstream pressure 33. Particularly, such a calibrated reference pressure 35 is robust against fluctuations of an ambient pressure. Furthermore, the carrier gas supply unit 50 in accordance with FIG. 1 may be combined with a purging system and/or an effluent collection system without compromising the obtainable measurement precision.

The second pressure sensor 34 has a higher precision than the first pressure sensor 32. Thus, the second pressure sensor 34 is apt to adjust the downstream pressure 33 at an increased precision. The function of the first pressure sensor 32 does not require such a level of precision and is therefore a relatively simple and cost-effective sensor 30. The first and second pressure sensor 32, 34 are appropriately chosen for their respective functions.

The valve circuit 25 is connected to a control interface 37 that is configured to establish a connection to a control unit 40. The control unit 40 encompasses a control enclosure 42 in which a master control circuit 44 is accommodated. The control enclosure 42 is self-contained and separate from the pressure module 20. Substantially any exchange of fluids between the respective inside of the control enclosure 42 and the pressure module 20 is inhibited. The master control circuit 44 is connected to an intrinsic safety barrier circuit 44 that serves as an interface to the control interface 37 of the pressure module 20. Both power and signals 45 are being transferred between the control unit 40 and the pressure module 20 through the intrinsic safety barrier circuit 46. In particular, this power and these signals 45 allow for actuating to valve 24 and communication with the sensors 30, which comprise the first and second pressure sensor 32, 34. The intrinsic safety barrier circuit 46 comprises multiple electronic components that are configured to limit a voltage supplied to the control interface 37.

The energy supplied to the control interface 37 is limited to a maximum energy that does not allow for ignition inside the pressure module 20 or valve 24. Even if gas 15, especially hydrogen, leaks into pressure module 20, there will be insufficient energy to cause an ignition. The disclosed gas analyzer 10 is apt for using flammable gases like hydrogen as a carrier gas 15 for operation. Furthermore, at least a portion of the gas analyzer 10 shown in FIG. 1 is mirrored in a set of data points 62 that belong to a computer program product 60. The computer program product 60 is a digital twin 65 of at least a portion of the gas analyzer 10. The computer program product 60 is configured to simulate the operational behavior of the gas analyzer 10.

Figure 2:
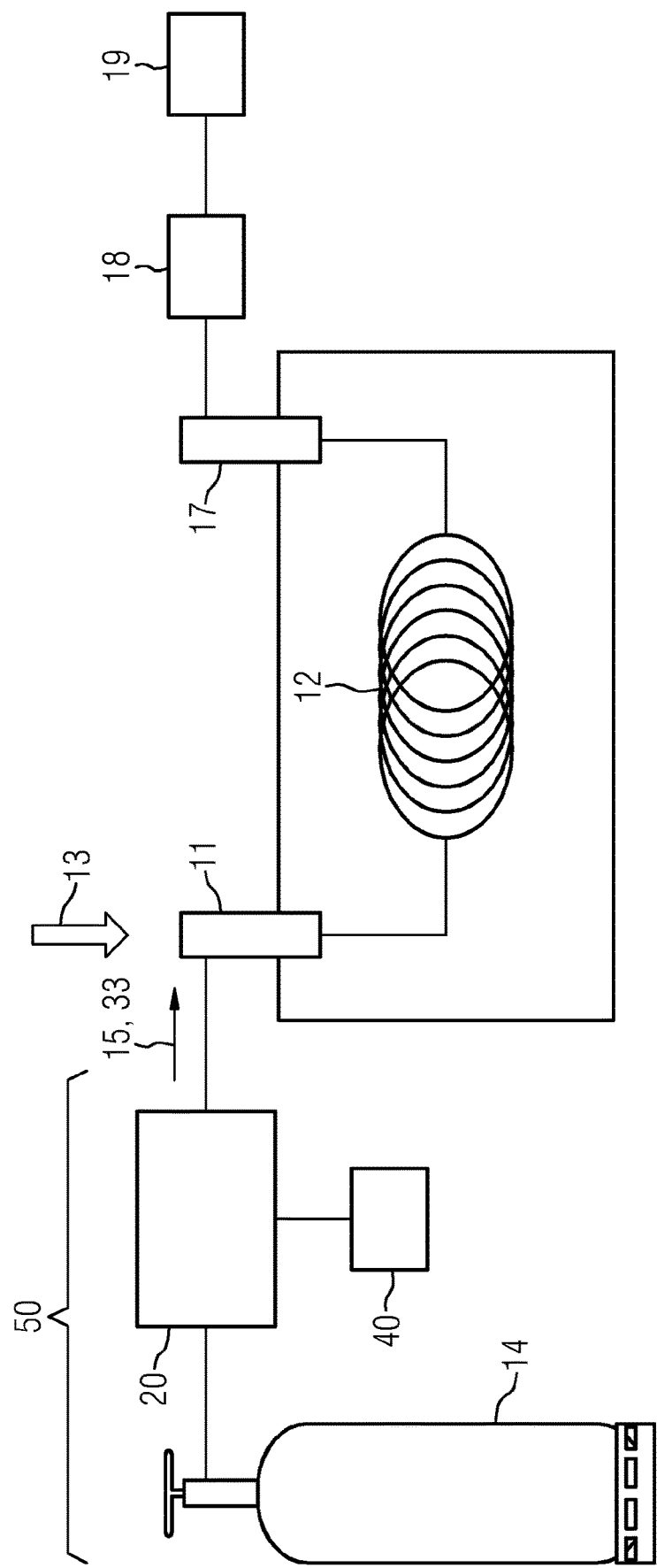
FIG. 2 an overall layout of a second embodiment of the inventive gas analyzer.

FIG. 2 shows an overall layout of the second embodiment of the claimed gas analyzer 10 that is a gas chromatograph. The gas chromatograph comprises a carrier gas supply unit 50 that provides a carrier gas 15 for a chromatographic analysis that is to be performed with the gas analyzer 10. The carrier gas 15 is taken from a gas reservoir 14 and fed through a pressure module 20 that is controlled through a control unit 40. The gas 15 from the gas container 14, i.e., the carrier gas 15, is fed to an injector 11 where it is mixed with a chromatographic sample 13, which is to be analyzed in the chromatographic process. The mixture of the chromatographic sample 13 and the carrier gas 15 are supplied to a separation column 12 that splits up the chromatographic sample 13 into its constituents. The chromatographic sample 13 travels with the carrier gas 15. As a result, the dedicated volume of the chromatographic sample 13 is determined by the downstream pressure 33 that is regulated in the pressure module 20. The constituents of the chromatographic sample 13 are analyzed in a detector 17 that detects at least one physical property of multiple constituents of the chromatographic sample 13. Signals from the detector 17 are amplified in an amplifier unit 18 and supplied to a data processing unit 19. Based on the amplified signals from the amplifier unit 18, the data processing unit 19 can identify and quantify multiple constituents of the chromatographic sample 13. The carrier gas supply unit 50 is configured in accordance with the carrier gas supply unit 50 as shown in FIG. 1.

Furthermore, at least a portion of the gas analyzer 10 shown in FIG. 2 is mirrored in a set of data points 62 that belong to a computer program product 60. The computer program product 60 is a digital twin 65 of at least a portion of the gas analyzer 10. The computer program product 60 is configured to simulate the operational behavior of the gas analyzer 10.

Figure 3:
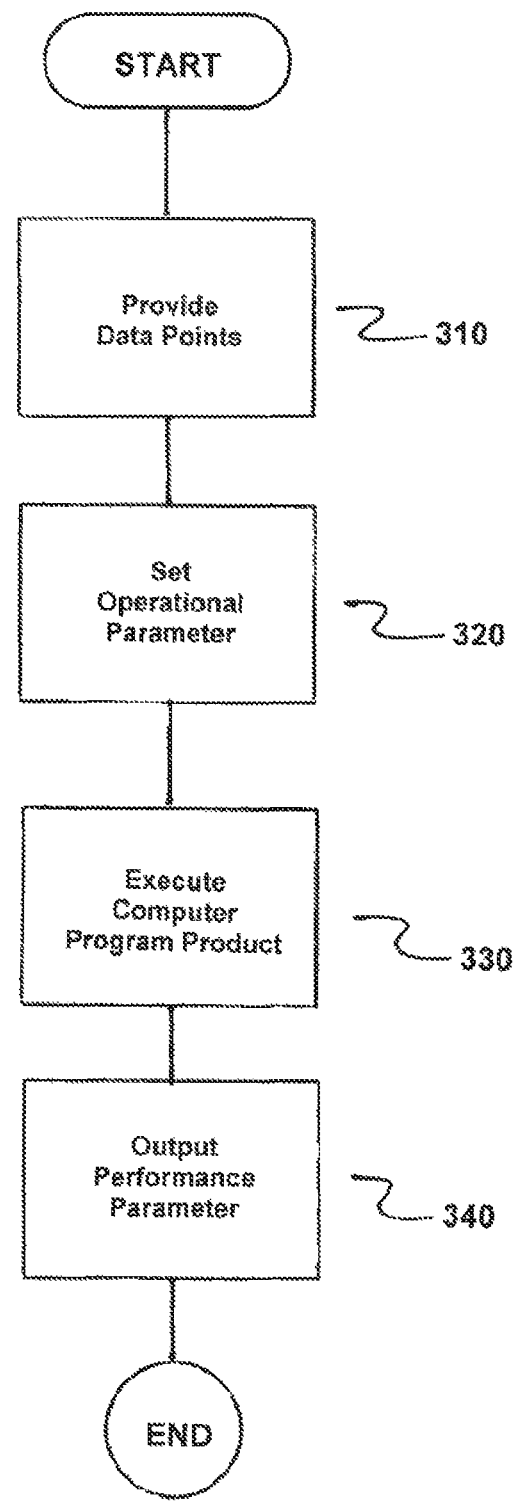
FIG. 3 is a flowchart of the method in accordance with the invention.

FIG. 3 is a flowchart of the method for simulating the operational behavior of a gas analyzer 10 comprising a self contained pressure module 20 that at least partially encloses a pipe 22 for a gas 15, at least one sensor 30 and a valve 24 that comprises a valve portion 28 and a solenoid portion 26, where the at least one sensor 30 and the valve 24 are operable via a master control circuit 44. The method comprises a) providing a set of data points 62 that mirror a functionality of at least at portion of the gas analyzer 10 that is to be simulated, as indicated in step 310.

Next, b) at least one operational parameter that defines an operational behavior that is to be simulated is set, as indicated in step 320.

Next, c) executing a computer program product 60 that is configured to emulate the operational behavior of the gas analyzer 10 is executed based on the set of data points 62 combined with the at least one operational parameter to determine at least one performance parameter, as indicated in step 330.

Next, d) the least one performance parameter is output to either a user and/or a data interface, as indicated in step 340.

In accordance with the invention, the master control circuit 44 is accommodated in a self-contained control enclosure 42 that separates the master control circuit 44 from the pressure module 20 with the valve 24 and the at least one sensor 30, where the valve 24 and the sensor 30 are accommodated in the pressure module 20.

Thus, while there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps that perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A gas analyzer comprising:
a self-contained pressure module that encloses a pipe for a gas,
at least one sensor; and
a valve that comprises a valve portion and a solenoid portion, the at least one sensor and the valve being operable via a master control circuit;
wherein the master control circuit is accommodated in a self-contained control enclosure, which separates the master control circuit from the pressure module with the valve and the at least one sensor, the valve and the sensor being accommodated in the pressure module.

2. The gas analyzer according to claim 1, wherein the valve is at least partly accommodated in at least one of an encapsulation and a molding.

3. The gas analyzer according to claim 2, wherein the master control circuit comprises an intrinsic safety barrier circuit through which itthe master control circuit is connected to the at least one sensor and the valve.

4. The gas analyzer according to claim 1, wherein the master control circuit comprises an intrinsic safety barrier circuit through which itthe master control circuit is connected to the at least one sensor and the valve.

5. The gas analyzer according to claim 4, wherein the intrinsic safety circuit barrier comprises interfaces for at least one channel.

6. The gas analyzer according to claim 5, wherein the intrinsic safety circuit barrier comprises interfaces for at least four channels.

7. The gas analyzer according to claim 6, wherein the intrinsic safety circuit barrier comprises interfaces for at least six channels.

8. The gas analyzer according to claim 7, wherein the intrinsic safety circuit barrier comprises interfaces for at least eight channels.

9. The gas analyzer according to claim 1, wherein the pressure module is a non-explosion-protected enclosure.

10. The gas analyzer according to claim 1, wherein
the at least one sensor includes a first pressure sensor which is exposed to a gas pressure inside the pressure module,
the gas pressure serves as a reference pressure, and
the first pressure sensor is configured to detect a depleting gas supply.

11. The gas analyzer according claim 10, wherein the first pressure sensor is configured to measure an inlet manifold pressure for the pipe.

12. The gas analyzer according to claim 11, wherein the at least one sensor further comprises a temperature sensor for compensating thermal effects on the first pressure sensor.

13. The gas analyzer according to claim 10, wherein the at least one sensor further comprises a temperature sensor for compensating thermal effects on the first pressure sensor.

14. The gas analyzer according to claim 13, wherein the pressure module comprises a memory with a calibration data field for compensating the thermal effects on the first pressure sensor.

15. The gas analyzer according to claim 1, wherein the master control circuit is configured to provide at least sufficient energy to operate the valve.

16. The gas analyzer according to claim 1, wherein the at least one sensor comprises a second pressure sensor for measuring a pressure in thea tube downstream of the valve.

17. The gas analyzer according to claim 16, wherein the second pressure sensor is configured to be connected to a source of calibrated reference pressure.

18. The gas analyzer according to claim 17, wherein
the at least one sensor further comprises a first pressure sensor, and
the second pressure sensor has a higher precision than the first pressure sensor.

19. The gas analyzer according to claim 16, wherein
the at least one sensor further comprises a first pressure sensor and
the second pressure sensor has a higher precision than the first pressure sensor.

* * * * *